United States Patent [19]

Ozero

[11] Patent Number: 4,904,807
[45] Date of Patent: * Feb. 27, 1990

[54] SELECTIVE EXTRACTION OF ARGON FROM ETHYLENE OXIDE RECYCLE STREAM

[75] Inventor: Brian J. Ozero, New York, N.Y.

[73] Assignee: Scientific Design Company, Inc., Little Ferry, N.J.

[*] Notice: The portion of the term of this patent subsequent to Nov. 7, 2006 has been disclaimed.

[21] Appl. No.: 22,496

[22] Filed: Mar. 6, 1987

Related U.S. Application Data

[63] Continuation of Ser. No. 729,431, May 1, 1985, abandoned.

[51] Int. Cl.$^4$ ............................................. C07D 301/10
[52] U.S. Cl. ......................................................... 549/534
[58] Field of Search ........................................ 549/534

[56] References Cited

U.S. PATENT DOCUMENTS

| 3,083,213 | 3/1963 | Courter | 549/534 |
| 3,119,837 | 1/1964 | Kingsley et al. | 549/534 |
| 3,725,307 | 4/1973 | Brown et al. | 549/534 |
| 4,230,463 | 10/1980 | Henis et al. | 55/16 |

FOREIGN PATENT DOCUMENTS

| 1055147 | 1/1967 | United Kingdom | 549/534 |
| 1191983 | 5/1970 | United Kingdom | 549/534 |
| 1321095 | 6/1973 | United Kingdom | 549/534 |

OTHER PUBLICATIONS

R. P. Rastogi et al., *J. of Membrane Science* (1978), "Thermoosmotic Studies on Argon Gas and Binary Gaseous Mixtures . . . ," 4, pp. 1–15.
W. A. Bollinger et al., CEP (Oct. 1982), "Separation Systems for Oil Refining and Production," pp. 27–32.
R. S. Narayon et al., paper presented at the Permian Basin Regional Meeting of the Gas Producers Association, 5/6/82, Midland, Tex., pp. 1–18.

*Primary Examiner*—Glennon H. Hollrah
*Assistant Examiner*—Mark W. Russell
*Attorney, Agent, or Firm*—Kenneth H. Johnson

[57] ABSTRACT

The invention relates to an improved process for production of ethylene oxide which minimizes unreacted ethylene losses through the use of semi-permeable membrane units, thereby allowing an effective, selective removal of argon from the process cycle gas, without significant ethylene losses.

4 Claims, 1 Drawing Sheet

SELECTIVE EXTRACTION OF ARGON FROM ETHYLENE OXIDE RECYCLE STREAM

This application is a continuation of application Ser. No. 729,431, filed 05/01/85, now abandoned.

BACKGROUND OF THE INVENTION

1. Field of the Invention

This invention relates to an improvement in the process for the production of ethylene oxide through the silver catalyzed vapor phase oxidation of ethylene and, more particularly, to an economic process for producing ethylene oxide which minimizes unreacted ethylene losses through the use of semipermeable membrane separation units, thereby permitting an effective, selective removal of argon diluents from the process cycle gas, without significant ethylene losses.

2. Description of the Prior Art

The production of ethylene oxide is one of the most important commercial reactions in the world, with a current annual production of about eight million tons/year worldwide. Frequently the operation of a process of this magnitude within the realm of commercial practicality can often depend upon the ability to increase, even by only relatively small amounts, the ethylene oxide yield or, conversely, the ability to reduce, even by only relatively small amounts, the costs of a variety of essential elements of the process.

In one major embodiment of the process, the oxygen supplied for reacting with ethylene is obtained from an expensive oxygen source providing essentially relatively pure oxygen, i.e., 95+%, along with a substantially lesser but yet significant fraction of one or more diluents, e.g., nitrogen, argon and the like. When added to the process cycle gas, usually in conjunction with a makeup ethylene stream, the oxygen and ethylene mix with a controlled amount of other diluents, other reaction products and contaminants, i.e., carbon dioxide, argon, nitrogen, methane, etc. The precise concentration of the ingredients which can be included is a significant consideration in determining the composition of the reaction gas since the prior art has had no economic way of selectively purging some of these impurities, particularly nitrogen and argon, without also losing large amounts of valuable feed gases, i.e., ethylene. In commercial scale plants excess $CO_2$ is usually chemically absorbed from the reaction recycle gas by contacting the gas stream with a hot potassium carbonate solution, stripping out the $CO_2$ with steam, and venting it into the atmosphere with a minimal loss of ethylene. Although such absorption units are expensive and also require significant amounts of energy during operation, they are still economically justified by the reduction in ethylene losses which they provide. In the past the art has controlled the concentration level of diluents such as argon and nitrogen by a less expensive purge type system, i.e., a venting or bleeding step, which unfortunately also results in the loss of a substantial amount of ethylene and therefore a reduced ethylene oxide yield.

A significant consideration in forming a suitable reaction gas composition, which typically is made of a majority of diluent ingredients, along with $O_2$ and $C_2H_4$, is to form a composition which avoids very high and unstable concentrations of oxygen and/or ethylene. Otherwise, a total combustion of the ethylene content, forming $CO_2$ and water as the reaction products, as well as the danger of an explosion caused by exceeding the flammability limit of the gas composition, can take place. The amount of argon present in the gas is particularly important regarding the flammability issue, since argon is a particularly ineffective component for reducing the flammability of the gas mixture. Thus, a method of selectively monitoring and economically removing certain components, particularly argon, without a substantial loss in reactant gas, particularly ethylene, has been a long felt need in the art.

U.S. Pat. No. 3,083,213 is an early teaching on the undesirability of the presence of argon, particularly regarding the flammability factor, in a disclosed ethylene oxide process. U.S. Pat. No. 3,119,837 discloses that methane can be a suitable diluent under certain circumstances in an ethylene oxide process. British Pat. No. 1,321,095 discloses an ethylene oxide process wherein ethylene levels as high as 40–80% by volume are permitted, and in which several diluents are controlled through means of a vent mechanism.

In copending case Ser. No. 729,340 of Brian Ozero, filed concurrently with the present application, the usage of semipermeable membranes to selectively remove $CO_2$ and argon from an ethylene oxide recycle stream is disclosed; the process of Ser. No. 729,340 employs a low purity oxygen feed stream and preferably does not utilize another unit operation to remove $CO_2$ from the system.

It is an object of this invention to provide a process for the selective removal of argon from the ethylene-oxygen recycle gas mixture.

It is another object of this invention to provide a process for the removal of argon, and accompanying maintenance of the process cycle gas at desired argon concentrations, without an accompanying substantial loss of ethylene, from the cycle gas.

SUMMARY OF THE INVENTION

Accordingly, the invention comprises an improved process for the production of ethylene oxide, comprising reacting ethylene with a substantially pure, e.g., at least 95 mole %, preferably 99+%, oxygen feed stream in the presence of a suitable silver-based catalyst, in a reaction zone under suitable temperatures, e.g., about 200° to 300° C., and super-atmospheric pressures, e.g., about 100 to 400 psia; the reaction occurring in the further presence of a suitable reaction gas mixture, i.e., about 5 to 50 mole % ethylene, 5 to 9 mole % $O_2$, 1 to 25 mole % Ar, 2 to 15 mole % $CO_2$, 0.2 to 1 mole % $H_2O$, and 20 to 60 mole % combined $CH_4$ and $N_2$; removing the ethylene oxide product from the reaction effluent gas mixture, e.g. in a scrubbing zone; removing a desired amount of $CO_2$, i.e. the average rate of removal preferably being substantially equal to the average rate at which $CO_2$ is formed during the process, from the reaction gas mixture, preferably by chemical absorption techniques; selectively removing a desired amount of argon, i.e., at an average rate substantially equal to the average rate at which argon enters the feed oxygen stream, e.g., removing about 0.01 to 0.5 mole % of the total reaction gas mixture; the removal occurring by passing a suitable amount, e.g., about 0.5 to 25%, preferably 2 to 5%, of the reaction gas mixture through a suitable semipermeable membrane unit, i.e., a membrane unit maintained at a pressure differential of about 10 to 400 psi, preferably about 100 to 250 psi; replenishing the depleted reactant gas mixture with fresh feed, i.e., $O_2$ and $C_2H_4$, and repeating the process cycle.

DETAILED DESCRIPTION OF THE INVENTION

Figure 1:
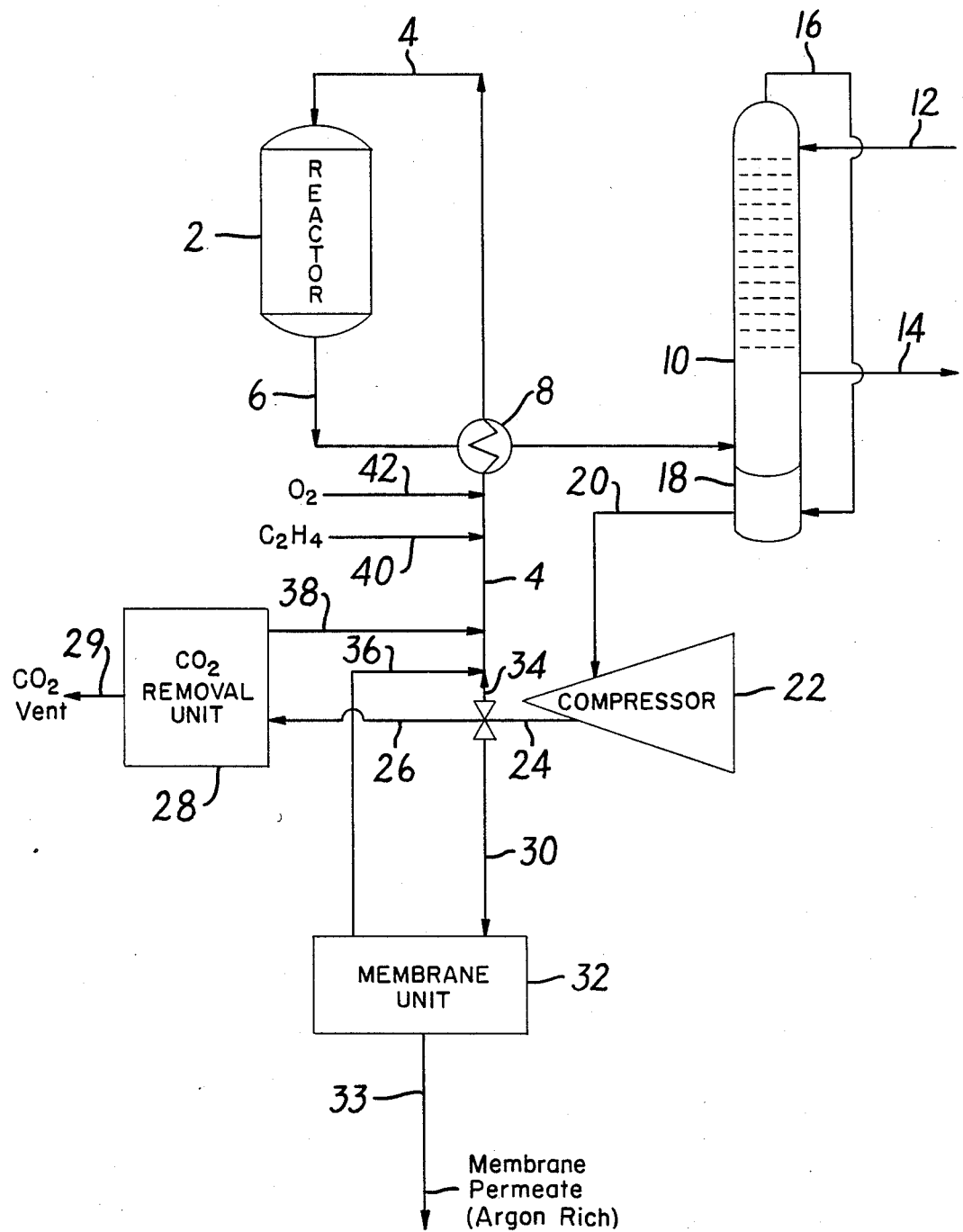
FIG. 1 sets forth a brief outline of the preferred process of the invention described.

Ethylene oxide today is produced commercially through the silver catalyzed, vapor phase incomplete oxidation of ethylene by molecular oxygen. Typically, the product ethylene oxide generally constitutes but a relatively small percentage of the total effluent stream leaving the oxidation reaction zone, e.g., about 1 to 3 mole %. The remainder of the reactor effluent comprises several diluents and reaction byproducts; the diluents functioning to negate the possibility of explosions and unwanted combustibility levels being attained during the reaction. If the so-called flammability limit, i.e., at which point the complete and rapid oxidation of ethylene to $CO_2$ and water can occur, is exceeded, the possibility of a serious explosion becomes a very real factor. Naturally, it is desired to operate under conditions which will maximize the conversion of ethylene to ethylene oxide yet avoid safety problems while maintaining an industrially acceptable reaction rate. In an effort to find such an optimum environment, gases such as nitrogen and methane are intentionally introduced and along with the reaction by-product carbon dioxide, and argon, which enter as an impurity in the oxygen feed, are maintained at predetermined concentrations in the recycle reaction gas. The goal of such composition setting is to find an optimum mixture which permits one to safely react maximum concentrations of oxygen and ethylene to form ethylene oxide, thus increasing the selectivity of the ethylene present to ethylene oxide.

Some of the diluents present in the recycle gas owe their origin to a gradual accumulation of impurities which are present in the reactant gas feed streams. This is certainly the case with argon, which enters the system as the major impurity present in the oxygen feed stream. The art has been unable to find a selective manner of removing the excess argon which builds up in the system, other than by simply purging a predetermined amount of the recycle gas mixture through a bleed stream which is then discarded. Such a purge gas, unfortunately, also contains a high ethylene concentration and results in a substantial ethylene loss, e.g., from about 0.1 to 5.0 mole % of the mixture, the magnitude of which depends on the argon content in the oxygen feed and the recycle gas stream.

Surprisingly, I have discovered that the addition of a suitable semipermeable membrane unit, e.g., either a single unit or a multi-stage membrane configuration, with a typical separator unit installed in a pressure vessel in a manner analogous to a shell and tube heat exchanger, can efficiently and selectively extract the argon from the remaining recycle mixture. The feed gas, i.e., a desired amount of the recycle gas stream, is first fed into the shell side of the separator. Due to the presence of a significant pressure differential, e.g., from about 20 to 400 psi and preferably from about 100 to 250 psi between the outer and inner sides of the membrane tube of fibre, the argon component desired to be separated more easily permeates through the membrane film as the gas stream traverses the length of the bundle. The resultant selective separation yields a permeate stream with a significantly higher, e.g., from about a 1.5 to 1 to a 50 to 1 argon to ethylene mole ratio on the inner side of the membrane tube or fibre than in the non-permeate, ethylene-rich shell side stream. The relative rate of permeation of each component present in the gas mixture is, in general, a function of the individual component's partial pressure differential across the fibre wall, as well as the component's solubility and diffusivity in the fibre. A preferred semipermeable membrane for use in the process is that sold under the trade name "PRISM" by Monsanto Company, St. Louis, Mo., but a wide variety of other such membrane units, as will be apparent to one skilled in the membrane art, are within the scope of the invention.

The process of the invention is of the type in which substantially pure molecular oxygen, in contrast to less pure oxygen or air, is employed as the makeup feed stock to replenish the oxygen consumed in the reaction. Purified oxygen having an oxygen content of at least about 95 mole % is introduced as a makeup stream into the system, the oxygen preferably being present in purity ranging from about 99.0 to 99.9 mole %. It is also desirable to operate in the range of high ethylene concentrations, in order to achieve a high ethylene selectivity to ethylene oxide, as this is clearly essential for commercial operation, and thus ethylene concentrations as high as about 40 to 50 mole % can be present in the recycle gas mixture. It is preferred, and almost essential for effective operation that the argon present in the oxygen makeup feed not exceed the range of about 0.1 to 5.0 mole %, typically about 0.5 mole % of the oxygen feed.

The gas mixture comprising the recycle reaction gas stream, in addition to the feed gases and the different impurities, also contains significant amounts of certain reaction products, e.g., the $CO_2$ formed as a major byproduct which has not been removed, water, and a small amount of unremoved ethylene oxide.

FIG. 1 sets forth a simplified outline of the preferred embodiment of the process. The system comprises a reactor unit 2 containing a suitable silver metal-based catalyst known to those in the art, e.g., such as that disclosed in U.S. Pat. No. 3,725,307, as well as many others, and through which an ethylene and oxygen containing mixture, entering through line 4 is passed, with fresh makeup ethylene and oxygen having been introduced earlier into line 4. A reactor effluent stream comprising ethylene oxide, unreacted feed components, various diluents and reaction byproducts is withdrawn from reactor unit 2 through line 6 and, after preferably being cooled in heat exchanger 8, preferably by warming the incoming reactor feed mixture in line 4, passes into a scrubbing unit (or another suitable separation unit) 10 wherein the gas mixture is scrubbed by contacting with an aqueous stream or another suitable ethylene oxide scrubbing agent entering through line 12 and eventually leaving the unit containing the absorbed ethylene oxide through line 14, from which stream the ethylene oxide is eventually extracted therefrom as product. The ethylene oxide-free effluent passes out of the scrubber through line 16 and passes through a mist separator 18 which removes any entrained liquid present. The scrubbed gas from separator 18 exits through line 20, and enters a compressor unit 22, where it is raised to a desired pressure, e.g., about 240 to 340 psia. The now pressurized gas stream passes through line 24 typically comprising about 5–15 mole % argon and from 5 to 15 mole % $CO_2$, whereupon the recycle stream is divided in order to remove the excess $CO_2$ and excess argon, with typically about 10 to 20% passing through line 26 into $CO_2$ removal unit 28, about 0.5 to 25% passing through line 30 into the semipermeable membrane unit 32, while the remaining gas stream passes through bypass line 34 leading back towards the reactor.

In membrane unit 32, the preferred design of which has been described above, a small, argon-enriched and ethylene-lean permeate stream (its argon content comprising about 0.001 to 0.1 mole %, preferably about 0.01% of the total reaction gas mixture) is separated from the entering gas mixture and suitably disposed of through line 33, such as by being fed to the incinerator or the like, while the non-permeate stream, preferably only slightly reduced in argon concentration, passes out of the membrane unit through line 36. Concurrently, the fraction of the recycle gas mixture which passes into $CO_2$ removal unit 28 is preferably treated for removal of $CO_2$ in a large commercial plant by conventional low ethylene loss means, e.g., a hot carbonate scrubber system, or the like, with the extracted $CO_2$-rich stream preferably vented through line 29, or otherwise suitably disposed of. The treated, $CO_2$-reduced fraction exits removal unit 28 through line 38 and preferably reunites with bypassed stream in line 34 and the exit gas from membrane unit 32 (line 36) to form the resulting cycle gas feed mixture present in line 4. About 5-25% of the $CO_2$ present is typically removed from the system in this manner. In the broadest embodiment of the invention the removal of argon, or $CO_2$, can take place at any point in the process cycle, starting from the removal of ethylene oxide product from the gas stream until prior to the addition of an ethylene makeup stream, although it is preferred to do so in the manner as earlier described. Other suitable locations for the argon membrane removal unit of particular note are on the line containing the gas stream 38 exiting the $CO_2$ removal unit, and also to recycle the non-permeate effluent from the membrane unit back to the compressor suction (line 20).

The treated recycle gas mixture is then preferably replenished by both ethylene and oxygen makeup streams 40 and 42, respectively; there being a great amount of discretion regarding the precise point of introduction, and such location forming no part of the invention. The stream preferably again passes through heat exchanger 8 and enters the reactor, the process is continued indefinitely.

The controlled oxidation reaction can be carried out at temperatures ranging from 150°-450° C., preferably in the range from about 200°-300° C. Suitable pressures which can be employed range from about 100 psia to about 400 psia, although higher pressures can be used if so desired. It is of course understood that a wide variety of other embodiments than the one disclosed are suitable for use in the invention.

I claim:

1. In a process for the production of ethylene oxide which comprises reacting a gas mixture comprising 5-50 mole % ethylene and 5-9 mole % oxygen in the presence of 1-25 mole % argon, 2-15 mole % $CO_2$, 0.2-1.0 mole % $H_2O$, and 20-60 mole % combined $CH_4$ and $N_2$ in a reaction zone at temperatures of 150°-450° C. and pressures of 100-400 psia over a silver catalyst, the source of oxygen feed to the reactor containing 0.1-5.0 mole % argon and at least 95 mole % oxygen, the improvement comprising the steps of:
   (a) recovering ethylene oxide from the reaction gas mixture, as in a scrubbing zone to provide a scrubbed gas which is essentially ethylene oxide free and containing about 5-15 mole % argon and from 5-15 mole % $CO_2$;
   (b) dividing said scrubbed gas into a first stream, a second stream and a third stream, said streams comprising 10-20%, 0.5-25% and 55-89.5% of the total scrubbed gas respectively;
   (c) removing about 5-15% of the $CO_2$ contained in said first stream by chemical absorption to provide a first recycle stream;
   (d) removing argon from said second stream in a separation unit having a semi-permeable membrane which selectively removes argon along with $CO_2$ at a pressure differential across the membrane of 20-400 psi to remove argon from said second stream at substantially the same rate at which it is added in the oxygen stream to provide a second recycle stream;
   (e) combining said first recycle stream, said second recycle stream and said third stream to form a combined recycle stream; and
   (f) replenishing the combined recycle stream by adding ethylene and oxygen to obtain the desired reaction gas mixture.

2. The process as claimed in claim 1 wherein the oxygen is supplied to the process as at least about 99 mole % $O_2$.

3. A process as claimed in claim 1 wherein the average rate at which $CO_2$ is removed by chemical absorption from the reaction gas is substantially equal to the average rate at which $CO_2$ is formed during the process.

4. In a process for the production of ethylene oxide which comprises reacting a gas mixture comprising 5-50 mole % ethylene and 5-9 mole % oxygen in the presence of 1-25 mole % argon, 2-15 mole % $CO_2$, 0.2-1.0 mole % $H_2O$, and 20-60 mole % combined $CH_4$ and $N_2$ in a reaction zone at temperatures of 150°-450° C. and pressures of 100-400 psia over a silver catalyst, the oxygen feed to the reactor containing 0.1-5.0 mole % argon and at least 95 mole % oxygen, the improvement comprising the steps of:
   (a) recovering ethylene oxide from the reaction gas mixture, as in a scrubbing zone to provide a scrubbed gas which is essentially ethylene oxide free and containing about 5-15 mole % argon and from 5-15 mole % $CO_2$;
   (b) removing about 0.5-4.0 % of the $CO_2$ contained in said scrubbed gas by chemical absorption to provide a lean $CO_2$ stream;
   (c) removing argon from said lean $CO_2$ stream in a separation unit having a semi-permeable membrane which selectively removes argon along with $CO_2$ at a pressure differential across the membrane of 20-400 psi to remove argon from said second stream at substantially the same rate at which it is added in the oxygen stream to provide a second recycle stream; and
   (d) replenishing the combined recycle stream by adding ethylene and oxygen to obtain the desired reaction gas mixture.

* * * * *